United States Patent [19]

Carlson

[11] Patent Number: 4,680,889
[45] Date of Patent: Jul. 21, 1987

[54] PROCESS FOR TREATING PLANTS

[76] Inventor: Danis R. Carlson, 708 119th La. N.E., Blaine, Minn. 55434

[21] Appl. No.: 802,477

[22] Filed: Nov. 27, 1985

Related U.S. Application Data

[63] Continuation-in-part of Ser. No. 792,617, Oct. 22, 1985, which is a continuation of Ser. No. 518,008, Jul. 28, 1983, which is a continuation of Ser. No. 286,260, Jul. 23, 1981.

[51] Int. Cl.$^4$ .......................... A01C 1/00; A01G 1/00; A01N 43/08
[52] U.S. Cl. .......................................... 47/58; 47/1.3; 47/DIG. 9; 71/89
[58] Field of Search ........................ 47/58, 1.3; 71/89

[56] References Cited

U.S. PATENT DOCUMENTS

| | | | |
|---|---|---|---|
| 3,703,051 | 11/1972 | Weinberger | 47/58 |
| 3,876,907 | 4/1975 | Widmayer | 315/208 |
| 3,902,273 | 9/1975 | Friedman | 47/58 |
| 4,055,915 | 11/1977 | Charnoe | 47/58 |

OTHER PUBLICATIONS

Biological Abstracts, vol. 57, No. 57126.
*Think*, vol. 34, No. 7.
Central Patents Index, Basic Abstracts Journal, Abstract No. 23358R.

*Primary Examiner*—Robert E. Bagwill
*Attorney, Agent, or Firm*—Merchant, Gould, Smith, Edell, Welter & Schmidt

[57] ABSTRACT

The present invention is a process for stimulating or inhibiting plant growth and includes the steps of applying a plant growth stimulant or inhibitor and subjecting the plant to high frequency sound waves.

14 Claims, No Drawings

PROCESS FOR TREATING PLANTS

This is a continuation-in-part Application of U.S. patent application Ser. No. 792,617 filed Oct. 22, 1985 which is a continuation of U.S. patent application Ser. No. 518,008 filed July 28, 1983, which is a continuation of U.S. patent application Ser. No. 286,260 filed July 23, 1981.

BACKGROUND OF THE INVENTION

The present invention relates to a process for stimulating plant growth and, more particularly, to stimulating plant growth by subjecting the plant to sound waves, with or without the application of growth stimulating solutions thereby opening the cell walls to assist the assimilation of the solution. The present invention further includes use of sound waves to assist in the assimilation of other solutions by plants. For example, one may decrease the level of herbicide to provide an effective killing dosage, thus minimizing pollution.

History reveals that many efforts have been made to increase growth rates in plants. This effort has generally been made to increase the food production from plants. For example, hybridizing has increased in a major way the yield obtained from such crops as corn, wheat, tomatoes, carrots and the like. Other efforts have been made in the development and use of plant foods and fertilizers. In some instances, fertilizer has been injected into the soil along with seed at the time of planting. It has also been known to spray fertilizer onto growing plants to feed systemically through the leaves.

More recently, effort has been directed toward hormone treatment of plants using gibberellin or gibberellic acid. It is recognized that gibberellin produces increased growth rates and increased plant sizes. There are nine types of gibberellin identified to date. Five of the gibberellins have been isolated from fungi such as *Phaseolus Multiflorus*. Three of the gibberellins have been isolated from higher plants, and one of the gibberellins have been isolated from both fungi and higher plants. The nine gibberellins have been designated types A-1 through A-9. The gibberellins are native plant growth hormones.

Sound waves have previously been used on plants to promote the growth and health of plants. A description of such use is found in the book entitled, "The Secret Life of Plants," written by Peter Thompkins and Christopher Bird and published by Harper and Row in 1973. The chapter entitled "The Harmonic Life of Plants" is of particular interest.

SUMMARY OF THE PRESENT INVENTION

The present invention is a process for treating plants with sound of a particular frequency to stimulate growth. Further the present invention is a process of treating plants with sound to force osmosis of growth promoting or growth inhibiting compositions. The process may include the steps of applying the growth affecting composition to the plant and subjecting the plant to sound waves while the growth affecting composition is disposed on said plant.

The growth promoting composition preferably includes gibberellin. The gibberellin may be of the type A-3. Various other growth promoting materials may be provided to the plant using the present process, for example, minerals, amino acids and the like. The growth promoting composition desirably is in the form of an aqueous solution. The water used in preparing the growth promoting solution desirably is free of materials that are detrimental to the plant, e.g. chlorine and fluorine. Detergent may be included in the solution to facilitate uniform distribution of the aqueous solution on the foliage of the plant. Growth inhibiting compositions may be similarly applied. A suitable inhibitory composition may be an aqueous solution of what is commonly referred to as 2,4D.

The sound used in the present invention may be produced using any of a variety of mechanisms. One technique that has proven suitable is the use of a recording, e.g. disc recordings and cassette recordings. Alternatively, electronic sound producing devices may be used.

DETAILED DESCRIPTION OF THE PRESENT INVENTION

In one embodiment of the present invention, plants are treated with sound waves desirably in the range of about 4 to 6 kilohertz. In another embodiment of the present invention the plants are treated with the combination of sound and growth promoting/inhibiting chemicals. The growth promoting chemicals, for example, are applied to plants in an effective amount to stimulate growth upon application of sound energy to the plant. Any technique may be used to apply the chemicals to the plants. In the case of applying chemicals as an aqueous solution to the foliage of plants, conventional spraying techniques may be used. In the case of applying the chemicals to seeds, the seeds may be wetted with an aqueous solution.

The growth promoting chemicals used in the present invention may include gibberellin, preferably of the type A-3. The chemicals may be dissolved in water which preferably is free of detrimental chemicals such as cholorine and fluorine. The gibberellin may be present in the solution in an amount of between 0.1 to 200 parts per million by weight. The preferred level is 0.5 to 100 parts per million.

The solution may include other materials which are beneficial to the plants. For example, derived proteinaceous materials such as amino acid chelated materials may be fed to the plants using the present process. Illustrative of such amino acid chelated materials are the Metalosates ® trace minerals from Albion Laboratories. These chelated proteinaceous materials are growth promoting. The proteinaceous materials may be used at a level of 1 teaspoon to 2 tablespoons per quart, preferably 1 troy ounce per gallon.

The growth promoting chemicals in the present invention may include seaweed extract. Illustrative of the sources of extract are seaweed of the types *Ascophyllum nodosum, Fucus vesiculosus* and *Fucus serratus*. A detailed discussion of production and conventional use of such seaweed extract is found in "Seaweed in Agriculture and Horticulture," by W. A. Stephenson. Seaweed extract is commercially available under the designation Maxicrop TM seaweed extract. The seaweed extract may be used as an aqueous solution including ½ teaspoon to 4 tablespoons per gallon, preferably 1 tablespoon per gallon.

The growth stimulating solution may include a detergent to facilitate uniform spreading of the solution on the plant, e.g. foliage. The detergent desirably is biodegradable. A commercially available suitable detergent is Basic H ®. The detergent may be used at a level of ¼ ounce per gallon.

The process may include use of lignite water (LA-Water XXX Normalizer ™ from CAW Industries of Rapid City, S. Dak.). The lignite water may be present in an amount of at least three ounces by volume per 100 gallons of solution, preferably four ounces to 100 ounces per 100 gallons of solution.

While the growth promoting material is present on the plant, the plant is subjected to sound waves of high frequency. The sound waves may be produced in any manner, for example, sound recordings or sound generating devices. The sound may be of a frequency of 4 to 6 kilohertz, preferably 4.7 to 5.3 kilohertz. The sound waves may be of a constant frequency; however, use of a variable frequency is preferred. For example, the plants may be subjected to sound waves which vary in frequency from 4.7 to 5.3 kilohertz. The period of one rise and fall in frequency may be from 0.1 to 0.5 seconds. To obtain the greatest benefit, it is essential that the plants be subjected to the sound waves while the growth promoting chemical or chemicals are present on the plant. It has been found that if the plants are first subjected to the sound waves, and then the sound waves are stopped and later the chemicals are applied, one does not obtain the present results. For example, it has been found that plants first treated with sound and later gibberellin type A-3 result in about 4 percent of the plants achieving exceptional growth, while if the gibberellin is present on the plant at the time of applying the sound, about 98 percent of the plants achieve exceptional growth. It is believed that sound waves serve to open the individual plant cells to increase the osmotic movement of the chemicals into the plant cells. The volume of the sound waves in the present invention may be at least 115 decibels, preferably 115 to 120 decibels. The duration of sound treatment is at least 15 seconds, preferably about 30 seconds to 30 minutes.

The present process increases both the rate of growth and the extent of growth of plants. In one experiment using the present invention, a cherry tomato plant was raised which was twenty feet in width and fifteen feet in height. The tomato plant yielded more than six hundred tomatoes. In another experiment, roses were treated and, rather than each side branch having single blooms, each side branch divided into additional side branches which resulted in multiple blooms. In a further experiment, a purple passion plant which usually grows to two feet in length actually grew to over five hundred times that length.

The present process for growth promotion has been found suitable for use on ornamentals, vegetables, fruits and the like.

The following are illustrative of various plants suitable for treatment under the present process:

soybeans, corn, sunflowers, dry edible beans, alfalfa, tomatoes, peppers, cucumbers, lettuce, zucchini, carrots, squash, Roses, African Violets, Orchids, Moss Roses, Purple Passion, Boston Ivy, English Ivy, Hawaiian Mylee, flowering shrubs, snowball bushes, fruit trees, weeping willows, silver maples, apples, bananas, oranges Aloe Vera, Jojoba, Guayule, Jerusalem Artichokes, Macadamia Nut Trees, leafy vines, flowers or plants normally grown indoors in pots, shrubs, bushes, flowers and ornamentals, orchids, lilies, and other tropical ornamental and vegetable or farm crops.

The present process for growth promotion in most instances produces an increase in growth rate of at least 15 percent and in some instances has resulted in a plant size increase of over five hundred fold. Seed production has been increased by two to three hundred percent and more. The seeds are larger than normal and carry forward the increased production and growth rates. The treated plants have a greater resistance to drought and frost.

The particular method of application of chemicals may vary. In some instances, the plant foliage may be treated; in other instances, the roots; and in still others, the seeds are treated prior to germination. Cuttings may be rooted in a solution according to the present invention while sound is applied.

The present process for growth inhibition has been found suitable for any undesirable plant growth such as grasses, rag weed, button weed and the like. The present process for plant life inhibition may be carried out using any growth inhibitor together with the sound treatment. For example, a conventional weed spray such as 2,4D may be used. The inhibitor may be used at a lower level of application and acts more rapidly than conventional use. For example, the herbicide concentration and thus application may be reduced by 5 to 75 percent.

EXAMPLE I (Purple Passion Plant)

The present invention was carried out by treating a purple passion plant with sound and a gibberellin solution. Potting soil was prepared by mixing 45 percent commercially available African Violet potting soil, 45 percent general potting soil (Woolworth's Black Magic ®), 4 percent sheep manure and 1 percent lime. This mixture was placed in a flower pot which had the lower portion filled with charcoal pieces. A small purple passion plant was purchased at a variety store and planted in the potting soil mixture. A gibberellin solution was prepared including ten parts gibberellin type A-3 and one million parts water. The water was free of chlorine and flourine. The gibberellin was applied by spraying to wet the leaves once each month. The gibberellin solution was applied while playing a recording to produce high frequency sound in the range of between 4 and 6 kilohertz. The sound was at a volume of about 115 decibels and was applied for over 30 seconds while the solution was present on the leaves. The plant grew to a length of over 1000 feet during an experimental period of two years. The high frequency sound is believed to open the stomata of the plant to enable forced osmosis of the gibberellin solution into the cells.

EXAMPLE II (Edible Yellow #2 Beans)

A fifty acre field of wind damaged edeble yellow #2 beans located in Northern Minnesota was treated according to the present invention by mixing by volume 150 ounces of Maxicrop ®, 300 ounces of amino acid, 6 ounces of Basic H ® surfactant, 12½ ounces of lignite water, and 120 ounces of gibberellin A-3 in 300 gallons of water. Fifty acres of beans were sprayed using a tractor equipped with a crop sprayer. The mixture was applied at a rate of six gallons per acre. The tractor carried a speaker which emitted a sound at 4.82 kilohertz per second at a volume of 115 decibels. Sound was applied to the plant for over 15 seconds while the plant was being sprayed and sound continued to affect plant as tractor and sprayer moved through the field for approximately 3½ hours. The average growth of the plants was two inches in seven hours whereas nontreated control plants showed no noticeable growth over this period. The treated plants produced one metric ton of beans per acre and the untreated control plants produced 1400 pounds per acre.

EXAMPLE III (Weeping Willow Tree)

A weeping willow tree was treated according to the present invention. The tree was five feet tall and had a trunk diameter of ½ inch at a time of planting and commencement of treatment. The tree was treated monthly for a period of seven years. One gallon of the treating solution contained by weight 0.5 ounces Maxicrop ®, 0.26 ounces lignite water, 1.0 ounce amino acid, and 30 parts per million gibberellin in water. The leaves of the tree were wetted once each month with the solution and sound of about 5 kilohertz per second was applied for about 20 minutes. The sound volume was about 115 decibels. Over a seven-year period, the tree grew to a height of over 36 feet and a trunk girth of 47 inches.

EXAMPLE IV (Weeping Willow Seedlings)

The process of the present invention was carried out on weeping willow seedlings. The seedlings were obtained as bare-rooted seedlings. All seedlings were planted in comparable soil and grown for one year without special treatment. The seedlings were equal in size after the year's growth. The seedlings were identified into four test groups, e.g. Groups A, B, C and D. Group A was retained as a control and did not receive special treatment during the second year. Group B was grown under conditions identical to Group A except Group B received treatment in accordance with the present invention. More specifically, the seedlings of Group B were treated with sound at a frequency of about 5 kilohertz at a volume of 115 decibels. While receiving the sound treatment, the seedlings of Group B were sprayed with a chemical solution made up from a concentrate. The concentrate included by weight 7.78 percent gibberellin A-3, 7.78 percent surfactant (Basic H ®), 7.78 percent Willard Water, 26.67 percent amino acid and 50 percent seaweed extract. The concentrate was diluted by mixing one fluid ounce of concentrate in one gallon of water. The solution was applied to Group B by wetting the leaves with solution and applying the sound treatment. The sound treatment continued for 30 minutes after the solution was applied to each seedling. The seedlings of Group B were treated in the following manner. The seedlings of Group C were grown in a manner identical to Group B except those seedlings only received the sound treatment and did not receive the chemical application. Group D was grown in a manner identical to Group B except the seedlings of Group D received only the chemical treatment and did not receive the sound treatment. The new growth, over the summer, was measured with random selection of ten branches from each group. The average growth of the branches in each group was as follows: Group A was 41 inches; Group B was 80 inches; Group C was 45 inches; and Group D was 69 inches per branch.

EXAMPLE V (Tomato Seedlings)

The present process was applied to tomato seedlings of the type Burpee Big Boy ™. Treated plant growth and production was compared with a control that received no special treatment. A sufficient number of plants were included in control groups were planted on May 1st. The beginning plant sizes were equal in the two groups and the growing conditions were the same for both groups. The treated group was subjected to sound treatment and chemical spray after 41 days, 51 days, 65 days, 81 days, 97 days, and 129 days following planting. The plants in the treated group received application of 5 gallons solution per acre. Sound was applied for five minutes before chemical application, during application and for five minutes following application. The sound was at a frequency of 4 to 6 kilohertz and at a volume of 115 decibels. The chemical solution composition was as set forth in Example IV. At 41 days the plants in both groups had an average heighth of 10 inches. At 51 days the treated plants had an average heighth of 18 inches and the control plants 14 inches. At 81 days the treated plants had an average heighth of 51 inches and the control plants 48 inches. At this point the treated plants had an average of 6 tomatoes per plant whereas the control plants had an average of 2 tomatoes and the latter tomatoes were about one-half the diameter of the former. At 129 days following planting, the treated plants were 77 inches in heighth and the control 50 inches. The treated plants had an average of 7 tomatoes and the control had an average of 3. The treated tomato fruit was twice the size of the fruit from the untreated. The growth was observed as follows:

TABLE

| Growth Period Elapsed | Control Plant Height (Inches) | Treated Plant Height (Inches) | Percent Increase Over Control |
| --- | --- | --- | --- |
| 41 days | 10 | 10 | |
| 51 | 14 | 18 | 28% |
| 65 | 24 | 33 | 37.5% |
| 81 | 44 | 51 | 15.9% |
| 97 | 48 | 69 | 43.75% |
| 129 | 50 | 77 | 54% |

EXAMPLE VI (Boston Ivy)

The present process was applied to a Boston Ivy plant and the growth was compared with a control which only received sound treatment. Both plants were 2 feet in length at commencement of the test. The treated plant was sprayed with the present chemical on the following dates, June 10 and 20, July 4 and 16, August 1 and September 2. The plants both received the same sound application of 10 minutes following the application of chemical to sprayed plant. On October 22 the plant treated with sound only was 12 feet 10 inches and the plant treated with the combination of sound and chemical was 19 feet 9 inches in length.

EXAMPLE VII (Jerusalem Artichokes)

Jerusalem artichokes of the variety Mammouth French White ™ were treated according to the present invention and compared with a nontreated control group. All specimens were planted on the first day of May. The treated group was treated by application of sound at a frequency of between 4 and 6 kilohertz for five minutes and while the sound continued the plants were wetted with the solution described in Example 1. The sound treatment was continued for five minutes following application of chemical. A control group was grown under identical conditions except it received no chemical or sound treatment. On the dates shown in the following table six random plants were measured in each group and the six were averaged to provide the results shown. A second control group was also grown but treated only with the chemical. The second control group was not measured but the tubers weighed for comparison. On each of the listed dates, six random samples of each group were sacrificed and the tubers weighed. The results were as follows:

| | Spray Plus Sound | | No Spray No Sound | | Spray No Sound |
|---|---|---|---|---|---|
| Date | Height (In.) | Tuber Wt. | Height | Tuber Wt. | Tuber Weight |
| 06/10 | 20" | — | 21" | — | — |
| 06/20 | 34" | — | 30" | — | — |
| 07/04 | 47" | — | 42" | — | — |
| 07/16 | 62" | — | 55" | — | — |
| 08/01 | 84" | 3 lbs. | 61" | ½ lb. | 1 lb. |
| 09/02 | 108" | 7 lbs. | 72" | 1 lb. | 4 lbs. |
| 10/22 | | 16 lbs. | | 6 lbs. | 11 lbs. |

The plants sacrificed on October 22 had 9 to 11 tubers on the plants treated with the combination of sound and chemical whereas, the plants which received no spray and no sound had either 3 or 4 tubers per plant.

EXAMPLE VIII (Cherry Tomatoes)

The effect of the use of sound in the present invention was treated by selecting nine uniform cherry tomato plants. The plants were each six inches in height. The plants were divided into three groups of three plants. Group 1 was treated with the solution described in Example I by spotting 50 microliters of solution over an area of 2.0 square centimeters on the second leaf from the top of the plant. The solution had been labeled with $Fe^{-59}$ isotope. The plants were subjected to 20 mv energy of sound for 15 minutes prior to application of the solution and for 15 minutes following such application. The sound was at between 4 and 6 kilohertz. Group 2 was treated in an identical manner except the sound treatment was omitted. The plants were held for 24 hours. Then a portion of the stem immediately above the treated leaf was removed from each plant in Group 1. The corrected counts per minute per milligram was 2.47±0.4. The stem portion immediately beneath the leaf was taken. The corrected counts per minute per milligram was 2.5±0.17. Group 2 plants were similarly analyzed. The corresponding values were 0.4±0.1 and 1.13±0.42 respectively. This shows a substantial effect in chemical uptake by the plants treated with sound over those not treated with sound.

EXAMPLE IX

The present invention was carried out to compare the effect of the chemical application together with and without sound application. A control without either chemical or sound was also carried out. Such testing was carried out by applying the composition described in Example I. The plants in each instance were grown from the Punch N' Grow TM product of Northrup King obtained from a commerical source. All plants emerged after one week. The various plants and groups were treated identically except for the fact that Group 1 was a control and did not receive either sound or chemical application. Group 2 received both sound and spray as described in Example I. The sound, however, was applied by a cassette recording played by a cassette player. The spray was applied by a hand-held spray gun. The sound was applied to the emerged plants for ½ hours three times a week. The chemical spray was applied once a week during one of the sound applications. Group 3 received the spray but no sound and Group 4 received sound but no spray. In all instances Group 2-4 provided more rapid growth than did Group 1. The combination of sound and spray provided greater growth than did either the spray alone or the sound alone. All Groups were started on February 26 and completed on March 19 for a total growth period of 21 days.

EXAMPLE X

A comparative test was carried out as described in Example IX except that started plants of Nephthytie and Oak Leaf Ivy were treated. The results of the 21 days growing period were as follows:

| | Nephthytis Height (cm) | | Oak Leaf Ivy Height (cm) | |
|---|---|---|---|---|
| Group | Start | Final | Start | Final |
| 1 | 22.0 | 24.5 | 13.5 | 16.0 |
| 2 | 18.5 | 20.0 | 15.0 | 19.0 |
| 3 | 15.0 | 17.5 | 13.0 | 15.0 |
| 4 | 18.0 | 19.75 | 15.0 | 18.0 |

The plants were again measured after 93 days. The results were as follows:

| | Nephthytis | | Oak Leaf Ivy | |
|---|---|---|---|---|
| Group | Start | Final | Start | Final |
| 1 | 22.0 | 26.5 | 13.5 | 28.0 |
| 2 | 18.5 | 24.0 | 15.0 | 35.0 |
| 3 | 15.0 | 24.5 | 13.0 | 26.5 |
| 4 | 18.0 | 22.0 | 15.0 | 30.0 |

Group 1 - no sound & no spray
2 - sound & spray
3 - spray no sound
4 - sound no spray

EXAMPLE XI

The present invention was carried out on the following plants substantially as described in Example IX comparing the present test specimen with controls which did not receive either sound or chemical. The sound was applied for at least 30 minutes.

|  | Planting | Dates Plant Sizes | | | | Final |
| --- | --- | --- | --- | --- | --- | --- |
| Plant | 11/17 | 11/24 | 12/1 | 12/8 | 12/15 | Weights |
| Soybeans (seeds) | | | | | | |
| **a. | | 1.6* | 4.0 | 5.7 | 6.0 | 1.7 oz. |
| ***b. | | 1.9 | 3.6 | 4.5 | 4.7 | 1.0 oz. |
| % increase over control | | −16% | +11% | +27% | +28% | +70% |
| Radish (seeds) | | | | | | |
| a. | | .7 | 1.0 | 2.4 | 5.3 | .8 oz. |
| b. | | 1.0 | 1.0 | 1.7 | 3.7 | .3 oz. |
| % | | −30% | 0% | +41% | +43% | +166% |
| Pole Bean (seeds) | | | | | | |
| a. | | 3.0 | 6.0 | 19.6 | 38.4 | 3.3 oz. |
| b. | | 3.0 | 3.3 | 6.6 | 9.6 | 2.4 oz. |
| % | | 0% | +82% | +197% | +300% | +38% |
| Onions (seeds) | | | | | | |
| a. | | 1.0 | 8.4 | 12.5 | 15.0 | 1.4 oz. |
| b. | | 1.0 | 8.6 | 10.3 | 12.8 | .7 oz. |
| % | | 0% | −2.4% | +21% | +17% | +100% |
| Peppers (plants) | | | | | | |
| a. | 6.8 | 7.2 | 8.0 | 9.4 | 9.4 | 2.8 lbs. |
| b. | 7.4 | 7.7 | 8.5 | 9.9 | 10.1 | 2.2 lbs. |
| % | −8.1 | −6.5 | −5.9 | −5.0 | −6.9 | +27% |
| Tomatoes (plants) | | | | | | |
| a. | 1.5 | 2.6 | 5.0 | 9.1 | 14.4 | 2.3 lbs. |
| b. | 1.5 | 2.9 | 4.6 | 7.2 | 11.8 | 2.2 lbs. |
| % | 0% | −10% | +8.7% | +26% | +22% | +4.5% |

*Plant measurements are in inches.
**a. Treated according to present invention
***b. Is the control plants without sound or spray.

EXAMPLE XII

Tests were conducted using ratio active isotope $Fe^{59}$ to compare the takeup rate of the growth stimulating solution of Example I with and without sound treatment. Nine 6-inch cherry tomato plants were selected as uniform as possible. Each member of Group 1 was spotted over a 2 square centimeter area of the second leaf from the top of the plant. Fifth microliters of solution was applied. The 2 square centimeters had 64,000 corrected counts per minute, or in other words 5 microcurries of $Fe^{59}$ isotope. Twenty microvolts energy sound at a frequency of between 4.7 and 6 kilohertz was applied for 15 minutes following the spotting. Group 2 was treated identical to Group 1 except the sound was not applied. Group 3 was treated the same as Group 1 except they did not receive either chemicals or sound treatment. The terminal leaf, opposite leaf, stem above point of application and stem below point of application was collected on all plants 24 hours post application. Corrected counts per minute per mg. were as follows:

|  | Group 1 | Group 2 | Group 3 |
| --- | --- | --- | --- |
| Terminal Leaf | 0.3 ± 0.2 | .67 ± .29 | 0.2 ± .16 |
| Opposite Leaf | .17 ± .12 | .47 ± .46 | .23 ± .06 |
| Stem Above | 2.47 ± 0.4 | .40 ± 0.1 | 0.6 ± .18 |
| Stem Below | 2.5 ± .17 | 1.13 ± .42 | 3.5 ± .22 |

EXAMPLE XIII

The present invention was carried out using a post emergent herbicide in combination with the application of sound on grassy weeds. The herbicide was Hoe-grass TM produced by Hertz Chemical, Ltd. The active ingredient was Diclofop Methyl. Twenty liters of concentrate containing 190 grams per liter active ingredient was diluted to 530 gallons by the addition of water. This dilution contained only 25 percent of the usual recommended active ingredient. The diluted solution was applied by a drawn boom-type sprayer at a rate of 10 gallons per acre while sound was applied at a frequency of between 4 to 6 kilohertz and at a transmitted volume of 115 decibels. Although the herbicide, together with sound, was applied at a level of only 25 percent of normal recommended application, the effect on inhibiting the grassy weeds, primarily wild oats, was essentially the same as full application using no sound.

EXAMPLE XIV

The present invention was carried out using a post emergent herbicide (Hoe-grass 2 TM by Hertz Chemical, Ltd.) in combination with sound on broad leaf weeds and grassy weeds. This herbicide included Diclofop Methyl and Bromoxynil having active ingredients of 310 grams per liter. Twenty liters of the herbicide concentrate were diluted with water to 540 gallons which is 25 percent of the usual recommended application concentration. The herbicide was applied at a rate of 10 gallons per acre while applying sound to 4 to 6 kilohertz and at a volume of about 115 decibels for at least 15 minutes. Satisfactory results were obtained on a cultivated field having substantial broad leaf and grassy weed infestation.

EXAMPLE XV

The present invention was carried out using Saber TM herbicide. Saber is a 1:1 mixture of Bromoxynil and META. The concentrate had 720 grams active ingredient per liter. Twenty gallons of Saber were diluted with water to 540 gallons and applied at the rate of 10 gallons per liter. This application is 25 percent of the recommended dosage. The application was accompanied with sound as described in Example XIV. The application satisfactorily inhibited the growth of weeds in a cultivated field having a mixture of common weeds.

EXAMPLE XVI the present invention was carried out as described in Example XIV, however using META Extamene. The active ingredient is META amine. The concentrate had 500 grams active ingredient per liter. Similar results were obtained.

EXAMPLE XVII

The present invention was carried out using Target ™. The active ingredient was a mixture of decamba, mecoprat and MCTA. The concentrate had 400 grams active ingredient per liter. Dilution and application was as described in Example XV. Similar results were obtained.

EXAMPLE XVIII

The present invention may be carried out using Ortho ™ Crab Grass killer. A concentrate having by weight 8 percent Octyl ammonium methane arsonate and 8 percent dodecyl ammonium methanearsonate. One tablespoon may be diluted with water to one gallon and applied to 200 square feet of lawn to effectively kill crab grass. Sound is applied at a frequency of between 4 to 6 kilohertz for at least 30 seconds following application of the solution.

EXAMPLE XIX

The present invention may be carried out using Ortho Weed-B-Gon ™ lawn weed killer. The active ingredients are 21.4 percent Butoxy propyl ester of 2,4-Dichlorophenoxyacetic acid and 10 percent 2(2,4,5-Trichlorophenoxy)propanoic acid by weight in the concentrate. One teaspoon of the concentrate may be diluted to one gallon with water. The solution may be applied by spraying on 167 square feet of lawn infested with such weeds as Buckhorn Plantain, Canada Thistle, Common Burdock, Common Plantain, Curly Dock, Dandelion, Dichondra, Ground Hog, Lawn Pennywort, Lippia, Morningglory, Wild Garlic and Wild Onions. Sound is applied as described in Example XVIII. Satisfactory results are obtained.

What is claimed is:

1. A process for treating plants to increase growth rates, wherein said process comprises applying to a plant an aqueous growth stimulating solution of gibberellin and then subjecting said plant to high frequency sound waves having a frequency of between 4 to 6 kilohertz while said gibberellin solution is disposed on said plant.

2. The process of claim 1 wherein said growth stimulating composition includes a chelated proteinaceous material.

3. The process of claim 1 wherein said gibberellin is of the type A-3.

4. The process of claim 3 wherein said gibberellin is present in said solution in an amount of from 0.1 to 200 parts per million by weight of the solution.

5. The process of claim 4 wherein said gibberellin is present in said solution in an amount of from 0.5 to 100 parts per million by weight of the solution.

6. The process of claim 1 wherein said gibberellin solution is applied by spraying said solution on the leaves of said plant.

7. A process for treating plants to promote growth of said plants, wherein said process comprises spraying plant foliage with a growth promoting gibberellin solution to wet the surface of said foliage, said gibberellin being of the type A-3, said gibberellin A-3 being present in said solution in an amount of 0.1 to 200 parts per million by weight based on the weight of said solution, and subjecting said plant foliage to high frequency sound waves to increase the receptivity of said foliage to said solution, said sound waves being of a frequency of between 4 and 6 kilohertz.

8. The process of claim 7 wherein the concentration of said gibberellin is between 0.5 and 100 parts per million.

9. The process of claim 7 wherein said sound waves are of a frequency of between 4.7 and 5.3 kilohertz.

10. The process of claim 7 wherein said sound waves are of a volume of at least 115 decibels.

11. The process of claim 7 wherein said sound is applied for at least 30 seconds.

12. The process of claim 14 wherein the frequency of said sound waves rises and falls to provide a varying pitch of 4 to 6 kilohertz.

13. A process for treating plants comprising wetting the plant with a growth promoting aqueous solution comprising 0.1 to 200 plants per million gibberellin, one troy ounce per gallon chelated proteinacious material, 1/16 to 4 tablespoons per gallon seaweed extract, 0.04 to 1 liquid ounce per gallon lignite water.

14. The process of claim 13 wherein said wetted plant is treated with sound at a frequency of 4 to 6 kilohertz at at least 115 decibels.

* * * * *

UNITED STATES PATENT AND TRADEMARK OFFICE
CERTIFICATE OF CORRECTION

PATENT NO. : 4,680,889
DATED : July 21, 1987
INVENTOR(S) : Danis R. Carlson

It is certified that error appears in the above-identified patent and that said Letters Patent is hereby corrected as shown below:

Column 1, line 41, "have" should be --has--;

Column 4, line 59, "edeble" should be --edible--;

Column 5, line 17, "a" should be --the--;

Column 6, line 8, after "groups" insert --and--;

Column 8, line 21, "hours" should be --hour--;

Column 8, line 23, "Group" should be --Groups--;

Column 9, line 38, "Fifth" should be --Fifty--;

Column 12, line 37, "14" should be --7--;

Column 12, line 42, "plants" should be --parts--;

Column 12, line 48, "at at" should be --of at--.

Signed and Sealed this

Fifteenth Day of December, 1987

*Attest:*

DONALD J. QUIGG

*Attesting Officer*   *Commissioner of Patents and Trademarks*